United States Patent [19]
Burden

[11] Patent Number: 5,890,488
[45] Date of Patent: Apr. 6, 1999

[54] COUPLING DEVICE AND SOUND RESONATING MEMBRANE FOR A STETHOSCOPE AND AN ENDOTRACHEAL TUBE

[76] Inventor: Brant S. Burden, 4231 Poppy Ave., Louisville, Ky. 40216

[21] Appl. No.: 909,445

[22] Filed: Aug. 11, 1997

Related U.S. Application Data

[63] Continuation-in-part of Ser. No. 518,076, Aug. 22, 1995, Pat. No. 5,655,518.

[51] Int. Cl.⁶ .................................................. A61M 16/00
[52] U.S. Cl. ................................ 128/200.26; 128/207.14; 128/205.23
[58] Field of Search ....................... 128/200.26, 207.14, 128/207.15, 205.23, 912

[56] References Cited

U.S. PATENT DOCUMENTS

| | | | |
|---|---|---|---|
| 3,493,075 | 2/1970 | Mendelson et al. | 181/131 |
| 3,499,435 | 3/1970 | Rockwell et al. | 600/484 |
| 3,734,094 | 5/1973 | Calinog | 600/380 |
| 4,198,963 | 4/1980 | Barkalow et al. | 128/53 |
| 4,327,720 | 5/1982 | Bronson et al. | 128/207.15 |
| 4,351,330 | 9/1982 | Scarberry | 128/207.15 |
| 4,383,534 | 5/1983 | Peters | 128/671 |
| 4,584,998 | 4/1986 | McGrail | 1278/207.15 |
| 4,607,643 | 8/1986 | Bell et al. | 128/715 |
| 4,917,107 | 4/1990 | Bell et al. | 128/715 |
| 4,953,547 | 9/1990 | Poole, Jr. | 128/203.12 |
| 4,996,141 | 2/1991 | Bacaner et al. | 128/207.14 |
| 5,056,514 | 10/1991 | DuPont | 128/207.14 |
| 5,181,508 | 1/1993 | Poole, Jr. | 128/203.12 |
| 5,357,946 | 10/1994 | Kee et al. | 128/200.24 |
| 5,562,078 | 10/1996 | Dzwonkiewicz | 128/207.18 |
| 5,655,518 | 8/1997 | Burden | 128/200.26 |

*Primary Examiner*—Aaron J. Lewis

[57] ABSTRACT

A coupling structure for placing a stethoscope and an endotracheal tube in gaseous communication, thus allowing an attending medical professional an enhanced ability to hear the breathing sounds of a patient in order to aid the medical profession to perform a nasal endotracheal intubation procedure while also providing the medical professional increased range of motion and protection from airborne pathogens and potentially dangerous bodily fluids, is described. A resonating membrane is positioned between the ends of the stethoscope and endotrachael tube to prevent air borne pathogens form passing into the stethoscope.

6 Claims, 4 Drawing Sheets

COUPLING DEVICE AND SOUND RESONATING MEMBRANE FOR A STETHOSCOPE AND AN ENDOTRACHEAL TUBE

This application is a continuation-in-part of application Ser. No. 08/518,076 filed Aug. 22, 1995 U.S. Pat. No. 5,655,518.

FIELD OF THE INVENTION

This invention relates in general to stethoscopes and, more particularly, to a device allowing a qualified medical professional to monitor breathing sounds while inserting a nasal endotracheal tube into a patient.

BACKGROUND OF THE INVENTION

The treatment of an individual suffering from emergency respiratory distress, especially in the field setting, is one of the hardest tasks facing a medical professional. Whatever the cause of the difficulty in breathing, the highest priority of the attending medical professional is to establish and maintain an unobstructed airway in the victim, thus insuring that an adequate amount of oxygen is being received by the patient.

Frequently, the preferred way of establishing an adequate supply of oxygen to a patient suffering from emergency respiratory distress is nasal endotracheal intubation, a procedure in which a breathing tube called an endotracheal tube is inserted into the trachea of a patient. For example, in the case of a trauma victim, a medical professional qualified to perform the nasal endotracheal intubation procedure, who will usually be a paramedic but might also be a physician, first places the head of the victim in a neutral position to insure against damage of the cerebral spine. While keeping the head of the victim in this neutral position, the medical professional inserts the endotracheal tube, typically, a flexible plastic tube open at either end, into a nare, or nostril hole, of the victim and pushes the tube through the nasal cavity, past the larynx, and finally into the trachea. The nasal endotracheal tube, which is usually used for this procedure, is modified to include a handle, which is usually ring shaped, attached to the tube by a string. Thus, the medical professional can use the handle to pull the tube into a shape necessary for navigating the tube through the nasal cavity and into the trachea. After insuring that the endotracheal tube is correctly fitted into the trachea, the medical professional uses a syringe to blow air into an air valve, which inflates a small bulb located near the end of the endotracheal tube, thus sealing the tube against the wall of the trachea. At this point, the medical professional can attach a bag valve device to an adaptor found on the exterior end of the endotracheal tube, thus placing the bag valve device in gaseous communication with the endotracheal tube, which insures that the victim is receiving an adequate supply of oxygen. Almost all endotracheal tubes will have this adaptor, which has a standard size tube extending from one side for attaching the bag valve device to the adaptor and, extending from the opposite side, a second tube of whatever size is necessary to fit within the diameter of the endotracheal tube, which comes in different widths based upon the size of the patient undergoing the procedure. After attaching the bag valve device, the medical professional can then treat any other medical conditions present. If the procedure was not performed while en route to a hospital, the victim will then be transported to a hospital.

While nasal tracheal intubation is the preferred way of establishing an unobstructed airway, a medical professional using this procedure often encounters various difficulties while trying to perform it, whether in the field or in a clinical setting. Since the procedure is a blind procedure, the attending medical professional must rely upon the intensity and characteristics of the breathing sounds exiting the patient to properly guide the endotracheal tube through the oropharynx and past the larynx into the trachea. Moreover, since the patient's ventilation may be interrupted by endotracheal intubation, the procedure should be completed within a maximum time of thirty seconds, more preferably fifteen to twenty seconds, to insure that the patient does not suffer any cell damage to the brain or other organs due to oxygen deprivation.

During this procedure, the medical professional usually is required to put his or her ear next to the exterior end of the endotracheal tube to listen for the intensity of the breathing sounds of the patient, using these sounds as a guide for properly placing the tube. This ear to tube method of performing the procedure has many disadvantages. First, the medical professional may not be able to hear the breathing sounds well enough to accurately guide the tube, either because the sounds are too faint or because of extraneous noise, such as sirens from emergency vehicles or the actions of bystanders. Second, the medical professional can be exposed to medical hazards exiting the body of the victim, including airborne pathogens and potentially dangerous bodily fluids, such as blood. Moreover, standard medical precautions, such as goggles, gloves, and masks, are not entirely satisfactory to prevent infection of the attending medical professional because the ear, and therefore the outer ear canal, must be exposed while performing this procedure. Pathogens or bodily fluids entering the outer ear canal can possibly cause infection there or elsewhere in the body.

It is also known in the prior art to remove the bell from the end of a single tube stethoscope cord and force the end of the stethoscope cord through the tubes of the adaptor on the exterior end of the endotracheal tube and into the exterior opening of the endotracheal tube to listen for the intensity of the breathing sounds while performing a nasal endotracheal intubation procedure. This cord into tube method increases the medical professional's ability to hear the victim's breathing sounds while providing increased protection from airborne and fluid borne pathogens.

However, there are still a number of significant disadvantages with the use of the cord into tube method. Since the stethoscope cord must be snugly inserted into the endotracheal tube for this method to be effective, it cannot be used with small diameter endotracheal tubes, which are used with children, because the cord is unable to fit within the diameter of the tube. Even if the attending medical professional tries to hold the end of the cord in the adapter with one hand, the quality of the breathing sounds will be greatly diminished; in addition, it will be difficult, if not impossible, to properly guide and insert the tube while using only one hand. Even when the cord does properly fit into the endotracheal tube, the flow of oxygen into the endotracheal tube, and thus, into the patient, is severely restricted, if not shut off entirely, during the time the procedure is being performed. Additionally, if it should become necessary to clear out blockage within the endotracheal tube by use of a remote suction device, the stethoscope cord must first be unwedged from the endotracheal tube. Because of the time limits for performing the nasal endotracheal intubation procedure, which will typically be ten seconds or more, is a critical drawback in using the cord into tube method. Finally, the stethoscope cord can easily become contaminated by any bodily fluids exiting the endotracheal tube, which will also have the effect of diminishing the ability of the medical professional to hear the patient's breathing sounds, and any airborne pathogens exiting the endotracheal tube will be constrained within the stethoscope cord, which increases the chances of the medical professional being infected by such pathogens. Thus, this method has also proven to be a less than satisfactory way of monitoring breathing sounds.

Various devices have been invented for connecting a stethoscope to an endotracheal tube to allow different types of medical personnel to better monitor patient breathing sounds. For example, U.S. Pat. No. 5,056,514, issued to "Dupont" on Oct. 15, 1991, describes a device that permits an anesthesiologist, or some other medical personnel, to monitor a surgical patient's breathing sounds with a stethoscope while anesthesia gas is being administered through an endotracheal tube placed visually through the surgical patient's mouth cavity and into the trachea. A stethoscope is connected to the device but is separated from the flow of gas by an impermeable membrane serving to prevent free flow of the anesthesia gas into the stethoscope tube. In order to hear the breathing sounds, it is necessary for the sounds to pass through the membrane for detection by a stethoscope attached to a chamber formed above the membrane.

OBJECTS OF THE INVENTION

Thus, it is an important object of the present invention to provide a device which improves the ability of an attending medical professional to hear and judge the intensity of a patient's breathing sounds while the medical professional is performing the nasal endotracheal intubation procedure on the patient.

It is still another important object of the invention to provide a device protecting an attending medical professional from potentially harmful bodily fluids and airborne pathogens while improving the medical professional's ability to hear and judge the intensity of a patient's breathing sounds, thus allowing the medical professional to accurately guide a nasal endotracheal tube into the patient's trachea in a nasal endotracheal intubation procedure.

SUMMARY OF THE INVENTION

The present invention contemplates the use of a device to serve as a coupling structure to couple an endotracheal tube and a stethoscope together so than an attending medical professional in a spaced apart relationship with respect to a patient can hear the intensity of the patient's breathing sounds while performing the nasal endotracheal intubation procedure on the patient. The coupling structure has a housing and two coupling elements attached to the housing, with one coupling element, in the form of a sleeve, being designed to slidably secure the coupling structure to an end of the endotracheal tube in a substantially airtight relationship and the other coupling element being designed to slidably secure the coupling structure to a stethoscope cord in a substantially airtight relationship, thus giving the medical professional a greatly enhanced ability to hear the patient's breathing sounds and protection from airborne pathogens and bodily fluids. As an additional feature of the invention, the housing of the coupling structure has an element with an opening, thus placing the air volume inside the housing in gaseous communication with the atmosphere, which allows a patient to breathe freely during the nasal endotracheal intubation procedure. A membrane adapted to facilitate or enhance the breathing sounds is placed in the coupling element coupling the stethoscope to the housing to further ensure that air borne pathogens from the patient do not travel up the tubes of the stethoscope.

DETAILED DESCRIPTION OF THE PREFERRED EMBODIMENT

Figure 1:
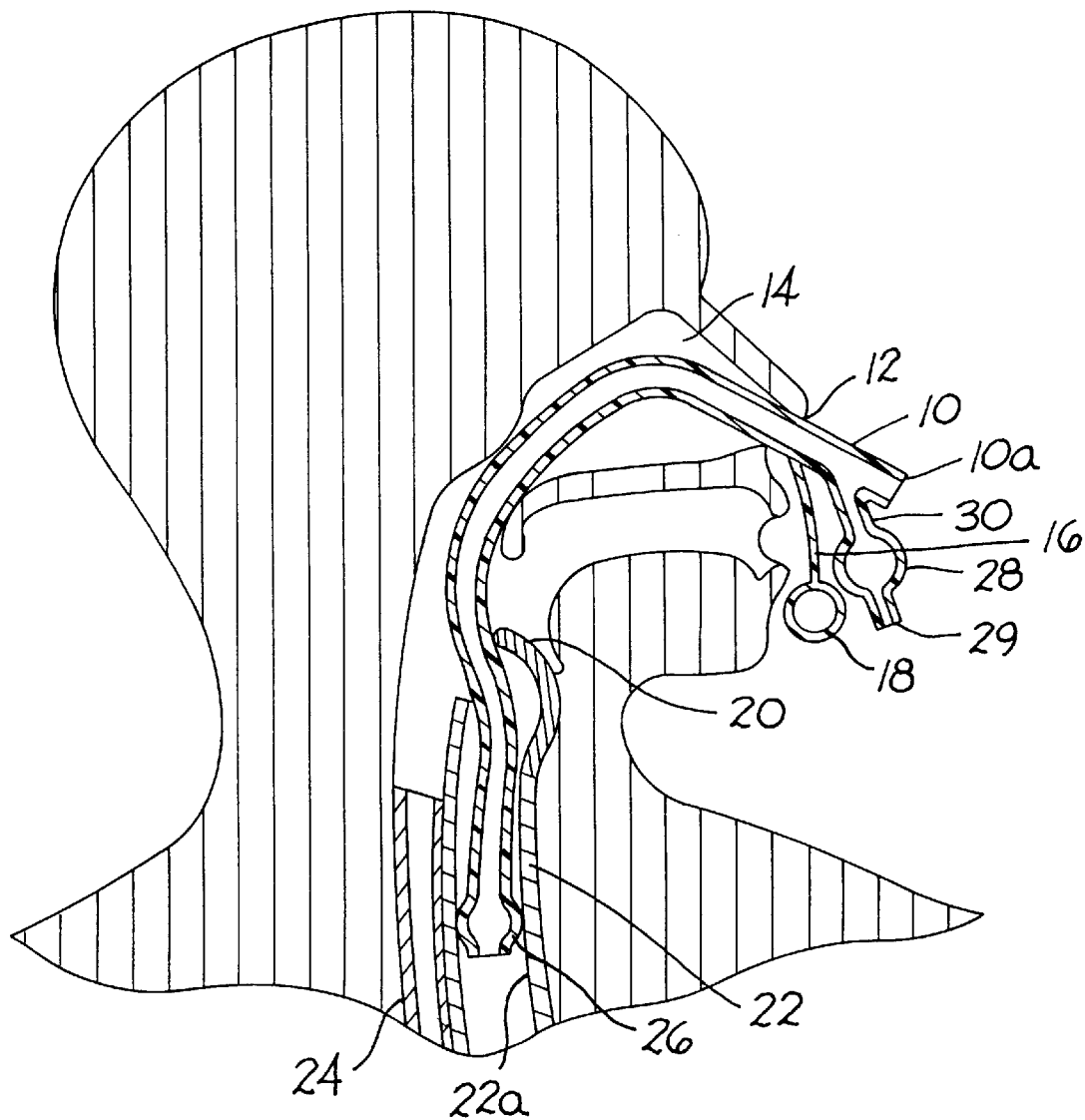
FIG. 1 is a side perspective view of a typical nasal endotracheal tube positioned in a patient.

To best describe a typical nasal endotracheal intubation, reference is made to FIG. 1 showing a nasal endotracheal tube 10 inserted into a nare (nostril opening) 12, through the nasal cavity 14, and past the epiglottis 20 into the trachea 22. The nasal endotracheal tube 10 has a string 16 attached near an exterior end 10a of the tube 10 to help bend and guide the tube 10 during the process of intubation and insure that the tube 10 does down the trachea 22 rather than the esophagus 24. The string 16 is shown with a ring-shaped handle 18 that assists the medical professional to pull the tube 10 into whatever shape is appropriate to guide the tube 10 into the trachea 22. The tube 10 also has an inflatable bulb 26 near the interior end 10b of the tube for sealing the tube 10 against the interior wall 22a of the trachea 22 after the tube 10 has been properly inserted; air is inserted into the bulb 26 by a medical professional using a syringe (not shown) to blow air into an air valve 29 of a tube member 30 which is in gaseous communication with bulb 26 through a hollow connecting tube (not shown). The tube member 30 is also equipped with a bulb 28, which begins to inflate when bulb 26 is full, thus letting the medical professional know when inflation of the bulb 26 has been completed.

Figure 2:
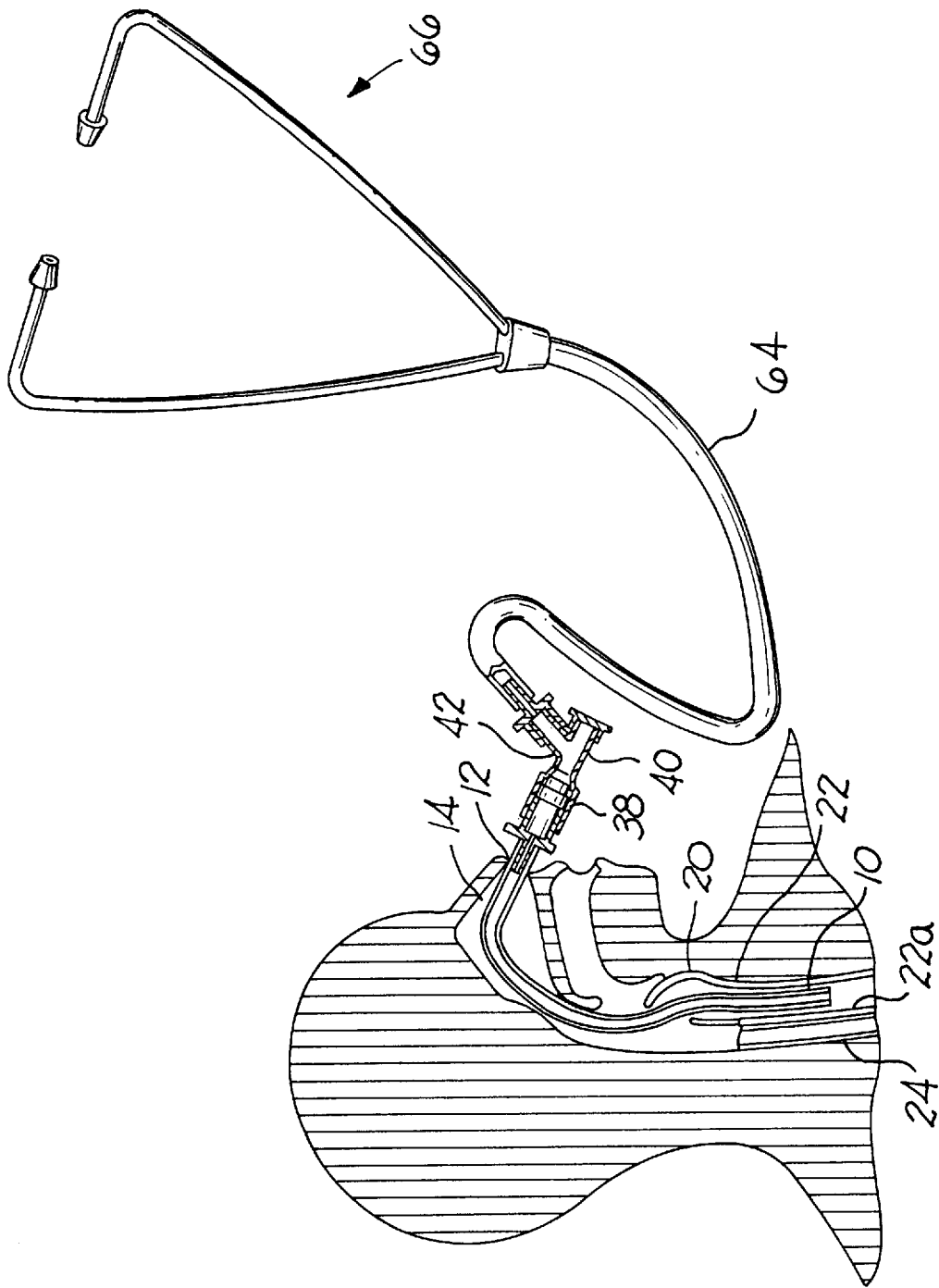
FIG. 2 is a side perspective view of a nasal endotracheal tube positioned in a patient, with an embodiment of the present invention coupling the tube with a stethoscope in an airtight relationship.
Figure 3:
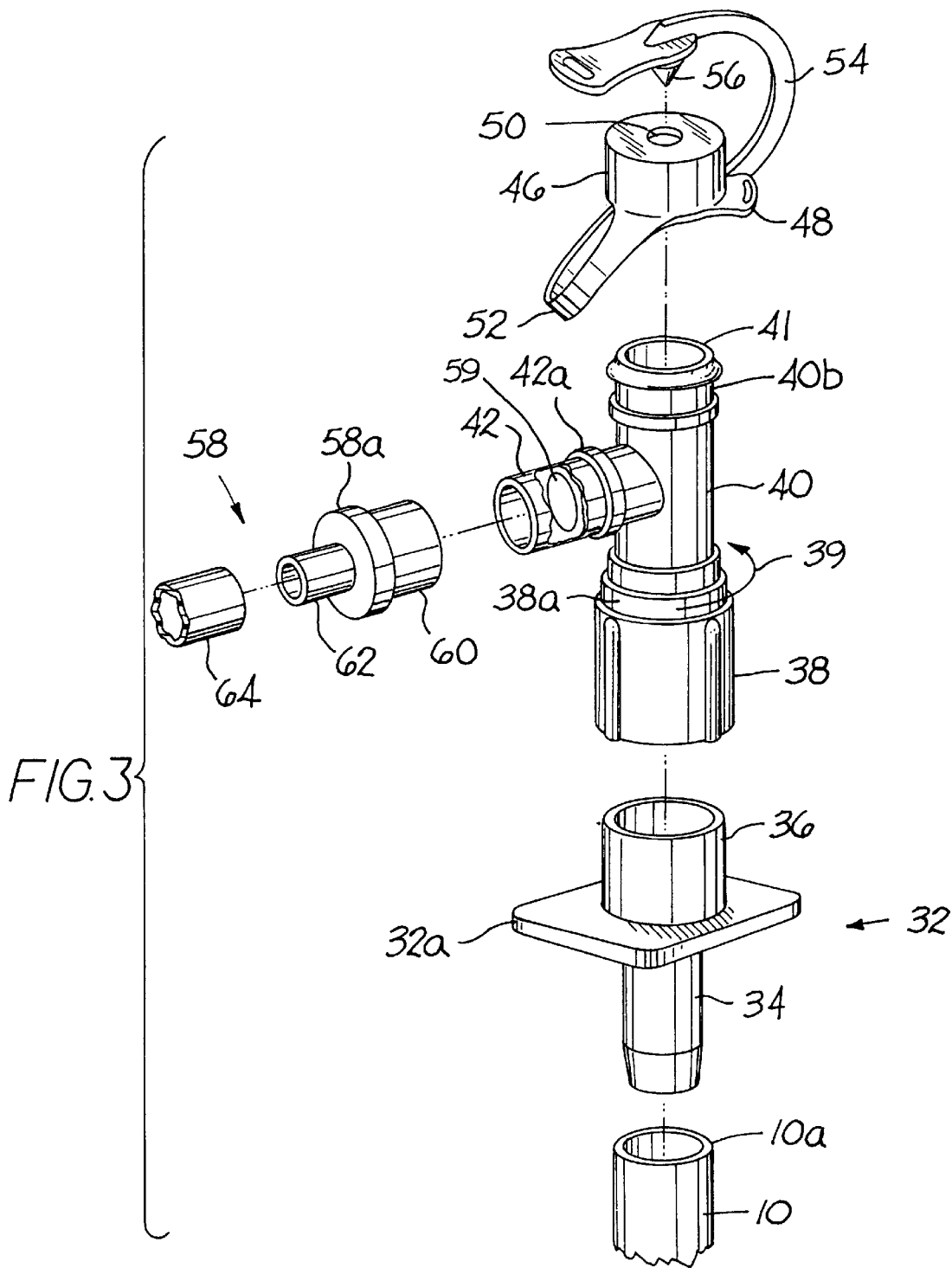
FIG. 3 is an exploded side perspective view of the preferred embodiment with a portion of the coupling member broken away to better view the positioning of a resonating membrane.

Reference is now made to FIGS. 2 and 3, which depict a cylindrically shaped housing shown by character number 40. The primary function of housing 40 is to couple an endotracheal tube 10 and a stethoscope 66 so as to meet the objectives set forth above. Housing 40 includes a tubularly shaped coupling member 42 that extends outwardly from the main body thereof and serves to couple housing 40 to an adaptor 58 which is itself detachably secured to the end of the cord 64 of the stethoscope 66. Adaptor 58 comprises an annular disk 58a integrally mounting a tubular element 60 extending from one side thereof and another tubular element 62 extending from the other side thereof. Tubular element 62 is slidably secured in an airtight relationship within the internal diameter of cord 64, while tubular element 60 fits over the external diameter of coupling member 42. The exterior surface of coupling member 42a which serves to abut the end of element 60. Adaptor 58 may be provided with various diameters of elements 60 and 62 as appropriate to match the various diameters of the stethoscope cords 64 that may be used and with the diameters of the associated coupling members of the housing 40. Coupling member 42 may be supplied with an internal acoustically resonating membrane 59 mounted across the internal cross section of member 42 as shown in the broken away portion of FIG. 3. Membrane 59 serves the dual purposes of enhancing sounds emanating from the patient and preventing the passage of airborne pathogens from moving from the patient into adapter 58 and moving up the stethoscope cords. Alternatively, a membrane could be placed across the cross-section of tubular member 60 close to the annular disk out of contact with the end of coupling member 42 as it slides into the large passageway of tubular member 60.

Figure 5:
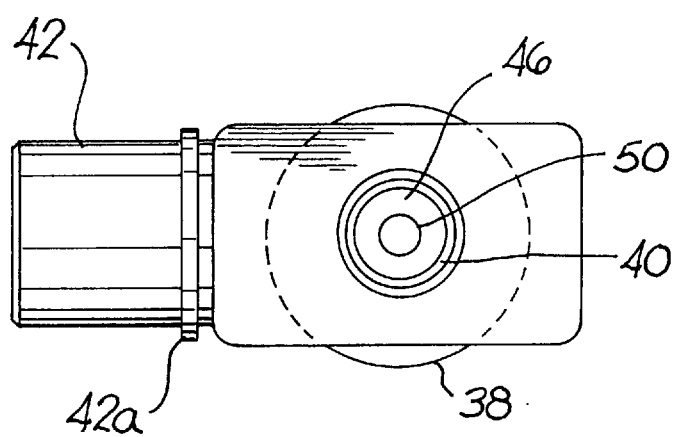
FIG. 5 is a bottom perspective view of the preferred embodiment.

As best seen in FIGS. 2 and 5, housing 40 is further provided at one end thereof with a circumferential groove (not shown) in the outer wall thereof for securing a tapered end 38a of a sleeve 38 having an internal rim complementary to the groove in a snap fit relationship which permits rotational movement of sleeve 38 with respect to housing 40. Adaptor 32 comprises a disk 32a integrally mounting a pair of oppositely extending tubular members 34 and 36 that respectively fit within the internal diameters of the end 10a of nasal endotracheal tube 10 and of sleeve 38 in airtight relationships. In this manner the entire housing 40 and the attached stethoscope 66 can be moved or be rotated in a plane, depicted by numeral 39, with respect to tube 10 as the situation may require without moving the tube 10 unduly.

As may be seen from FIGS. 2 and 3, the stethoscope 66 and the endotracheal tube 10 have direct gaseous communication with a volume defined by the interior of housing 40. This is important for two reasons: first, because it allows the attending medical professional to auscultate, or hear, the patient's breathing sound directly by use of the stethoscope 66 with no interference either from any structures inside the housing 40 or from outside noise, which is particularly a problem when using the ear to tube method of endotracheal intubation described previously. Second, since the housing 40 is provided with a tubular extension 40b defining an opening 41 which places the interior of housing 40 in gaseous communication with the atmosphere, which thus places the end 10a of the endotracheal tube 10 in gaseous communication with the atmosphere, the patient's breathing is not hindered in any way while the medical professional is listening for the breathing sounds with the stethoscope 66. If necessary, a suction catheter (not shown) from a remote suction device (not shown) can be inserted through opening 41 to clear out any blockage from the tube 10 without having to disconnect the coupling of the stethoscope cord 64 from the coupling member 42, thus saving time and allowing the medical professional to resume monitoring the patient's breathing sounds without having to again force the stethoscope cord 64 into the end 10a of the tube 10, as would be necessary with the cord into tube method of endotracheal intubation described previously.

Figure 4:
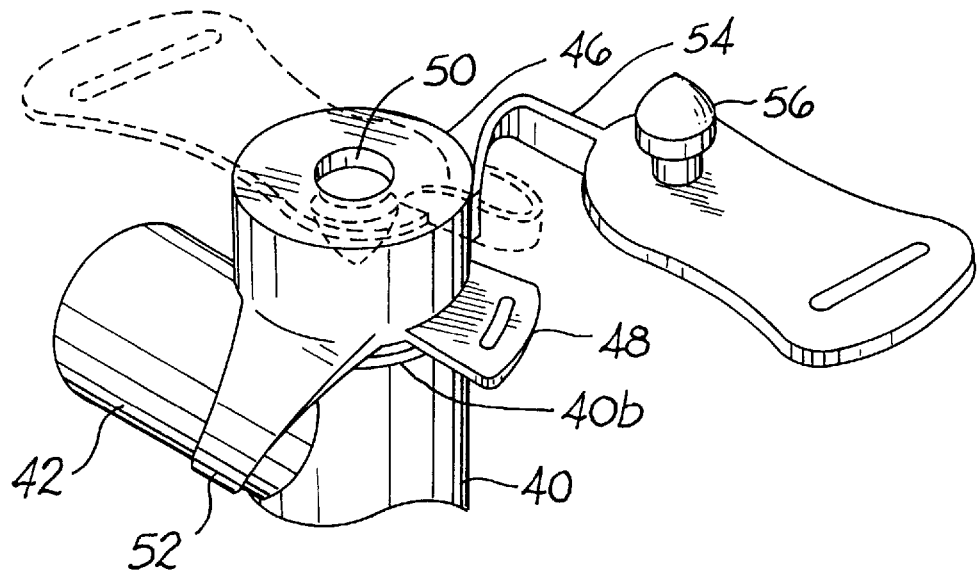
FIG. 4 is a top perspective view of the preferred embodiment.

As may also be seen in FIGS. 2–4, a cap 46 is positioned over the opening 41 of the housing 40. The cap has an aperture 50 of smaller cross-sectional area than the opening 41 of the housing. A tab 48 on said cap 46 allows for easy removal of the cap 46 whenever the medical professional must use a suction device (not shown). A securing strap 52, attached at one end of the cap 46, secures around the coupling member 42 behind the ridge 42a, and then attaches back to the cap 46. A plugging member 54 having a plug 56 for filling the aperture 50 of the cap 46 extends from one side of the securing strap 52. A primary function of this cap 46 is to serve as a sound amplifying component in the preferred embodiment because it reflects part of the breathing sounds exiting the tube 10 toward the coupling member 42 and into the stethoscope 66 through the stethoscope cord 64, thus allowing the medical professional to hear these sounds. This reflection of sound provided better detection of the breathing sounds, while the aperture 50 in the cap 46 allows the maintenance of gaseous communication between the atmosphere and the interior of housing 40. When maximum detection of the breathing sounds is desired, the plug 56 of the plugging member 54 may be temporarily inserted into the aperture 50. Alternatively, the aperture 50 can temporarily be partially or completely covered with a thumb (not shown) or a finger (not shown) for sound amplification. This aperture 50 also serves as an outlet for airborne pathogens exiting from the patient along a direct passage through the interior of housing 40 and past the opening 41 of the housing, thus shielding the medical professional from a direct line of contact with such pathogens.

As may be best seen in FIG. 4, the cap 46 is shown covering the opening 41 defined by the extension 40b of the housing 40. The strap 52 is shown secured around the coupling member 42, which is shown extending from the housing 40. The cap 46 is shown with the plug 56 out of the aperture, with phantom lines showing the plug 56 inserted into the aperture.

To better understand the use of a preferred embodiment during the nasal endotracheal intubation procedure, it is illustrative to describe a nasal endotracheal intubation procedure using an embodiment of the invention, again using the treatment of a trauma victim as an example. After placing the head in a neutral position to insure against damage of the cerebral spine, the medical professional can couple a sleeve of an embodiment of the present invention to the standard size tube of the adaptor on the exterior end of the endotracheal tube, and couple the stethoscope cord of a stethoscope with the bell removed, which the medical professional will usually have with him or her for performing this procedure, to the coupling member of the coupling structure. If necessary, a sealant of some sort could be used to keep the coupling between the tube and the coupling structure and the coupling between the stethoscope cord and the coupling structure substantially airtight. As an alternative to this method, the coupling structure could be already attached to a stethoscope cord, which would constitute an easily used and disposable unit for performing this procedure.

Whichever embodiment of the invention is chosen for use, the medical professional will then begin to insert the endotracheal tube into a nare of the victim, carefully listening through the stethoscope for the victim's breathing sounds, which, by their intensity and other characteristics, indicate to the medical professional the path that the endotracheal tube needs to take to properly enter the trachea. These sounds exit the end of the endotracheal tube and enter the volume defined by the housing, where part of the sounds will pass into the coupling member and part will travel toward the opening of the housing, where part of these sounds will be deflected by the cap on the opening of the back towards the coupling member of the housing for detection through the stethoscope. If any blockage in the airway is indicated through these sounds, the cap can be removed, either by a tab provided for this purpose or by simply pulling the cap off, and a suction catheter from some type of remote suction device can be inserted into the opening of the housing of the coupling structure into the endotracheal tube to clear out the blockage. Should bodily fluids begin to exit the victim through the endotracheal tube, the cap could again be removed to use a suction catheter; because of the fact that the stethoscope cord is superior in position and not in direct contact with the endotracheal tube, these bodily fluids will not contaminate or block the stethoscope cord. Instead, because of the effect of gravity, these fluids will tend to exit through the aperture of the cap, if it is in place, and through the opening in the housing of the coupling structure if the cap has been removed. After removal of the catheter, if used, the medical professional can resume placing the endotracheal tube, pulling the tube by the handle into whatever shape is necessary for navigating the tube through the nasal cavity and into the trachea. The medical professional is free to orient himself or herself in different positions around the victim, for example, to reach a medical bag, while still listening to the breathing sounds because of the rotational ability between the sleeve and the housing of the coupling structure. Also, because the coupling structure allows the medical professional to remain at a distance from the patient, the medical professional is afforded great protection from bodily fluids and airborne pathogens. After finishing the procedure and insuring that the endotracheal tube is correctly fitted into the trachea, the medical professional can remove the embodiment of the coupling structure from the endotracheal tube and throw it away, since it is desired to keep sterile conditions during this procedure. The medical professional can then seal the tube against the wall of the trachea by the method previously described, attach a bag valve device to the adaptor on the exterior end of the endotracheal tube, treat any other medical conditions present, and start transporting the victim to a hospital, if not already en route.

The present invention, as illustrated by the above description of the preferred embodiment and the sample description of its use in the field, clearly represents an advancement in the art of performing the nasal endotracheal intubation procedure. The invention allows a medical professional the ability to move around the patient if need be while performing the procedure; to keep a safe distance away from patients excreting bodily fluids and possible airborne pathogens, thus protecting the medical professional from possible infection; and provides a greater reception of the breathing sounds, all of which are significant advantages over the ear to tube method. Since the preferred embodiment allows free breathing by a patient because of the gaseous communication between the atmosphere and the endotracheal tube; the use of a remote suction device without having to unwedge a stethoscope cord from the endotracheal tube, assuming that the cord will even fit into the tube; and a path for bodily fluids and airborne pathogens to travel without entering the stethoscope cord, the preferred embodiment of the invention also provides a number of advantage over the cord into tube method. Also, the preferred embodiment allows for gaseous communication between the endotracheal tube and the atmosphere during use of the stethoscope by the medical professional performing the nasal endotracheal intubation procedure, while the stethoscope cord being wedged into the endotracheal tube will shut off substantially all of the air entering the endotracheal tube.

While a preferred embodiment of the invention has been illustrated and described in detail, it will be obvious to those skilled in the art that various modifications may be made to the disclosed embodiment without departing from the scope or spirit of the invention.

I claim:

1. A coupling structure adapted to place a nasal endotracheal tube and a stethoscope in gaseous communication while permitting the unimpeded breathing of a patient, thus allowing an attending medical professional, in a spaced apart relationship with respect to the patient, to listen for breathing sounds while performing a nasal endotracheal intubation procedure on the patient, said coupling structure comprising:
    a housing defining a substantially enclosed volume, with said housing further defining an opening for placing said volume in gaseous communication with the atmosphere;
    a sleeve connected in a substantially airtight relationship to said housing adapted to place said volume in gaseous communication with an end of a nasal endotracheal tube;
    a coupling member connected in a substantially airtight relationship to said housing adapted to place said volume in sound communication with a distal end of a stethoscope cord of a stethoscope, wherein said coupling member is positioned between said sleeve and said opening defined by said housing; and
    a membrane for resonating with sounds that emanate up said endotracheal tube into said volume, said membrane adapted to separate said stethoscope from being in gaseous communication with said volume when the distal end of said stethoscope cord is coupled to said coupling member.

2. The structure as recited in claim 1 in which said opening is defined by a first end of said housing and said sleeve is connected to a second end of said housing, said first and second ends positioned opposite to each other, thereby permitting insertion of a catheter through said opening directly into said sleeve.

3. A combination of a stethoscope, a nasal endotracheal tube, and a coupling structure coupling together a distal end of a stethoscope cord attached to said stethoscope and an end of said nasal endotracheal tube, said coupling structure having:
    a housing defining a substantially enclosed volume, with said housing further defining an opening for placing said volume in gaseous communication with the atmosphere;
    a sleeve connected at one end in a substantially airtight relationship to said housing for placing said volume in gaseous communication with one end of the nasal endotracheal tube, with said sleeve being coupled at another end to said end of said nasal endotracheal tube;
    a coupling member connected at one end in a substantially airtight relationship to said housing for placing said volume in sound communication with said distal end of said stethoscope cord, with said coupling member being coupled at another end to said distal end of said stethoscope cord, wherein said coupling member is positioned between said sleeve and said opening defined by said housing; and
    a membrane for resonating with sounds that emanate up said endotracheal tube into said volume, said membrane separating said stethoscope from being in gaseous communication with said volume.

4. The structure as recited in claim 3 in which said membrane is positioned in said coupling member.

5. A combination of a stethoscope, a nasal endotracheal tube, and a coupling structure coupling together a distal end of a stethoscope cord attached to said stethoscope and an end of said nasal endotracheal tube, said coupling structure having:
    a housing defining a substantially enclosed volume, with said housing further defining an opening for placing said volume in gaseous communication with the atmosphere;
    a sleeve connected at one end in a substantially airtight relationship to said housing for placing said volume in gaseous communication with one end of the nasal endotracheal tube, with said sleeve being coupled at another end to said end of said nasal endotracheal tube;
    a coupling member connected at one end in a substantially airtight relationship to said housing for placing said volume in sound communication with said distal end of said stethoscope cord, with said coupling member being coupled at another end to said distal end of said stethoscope cord;

a membrane for resonating with sounds that emanate up said endotracheal tube into said volume, said membrane separating said stethoscope from being in gaseous communication with said volume; and an adaptor for coupling said sleeve with said end of said nasal endotracheal tube while keeping said volume in gaseous communication with said end of said nasal endotracheal tube, said membrane being positioned within said adapter.

6. The structure as recited in claim 5, wherein said adaptor has first and second tubular members, with said first tubular member being sized to fit within said sleeve and said second tubular member being sized to fit within said end of said nasal endotracheal tube, said membrane being positioned in said first tubular member.

* * * * *